United States Patent
Tsai et al.

(10) Patent No.: US 10,820,814 B2
(45) Date of Patent: Nov. 3, 2020

(54) ELECTRONIC FITNESS DEVICE WITH IMPROVED LENS CONFIGURATION

(71) Applicant: Garmin Switzerland GmbH, Schaffhausen (CH)

(72) Inventors: Cheng-Yu Tsai, New Taipei (CN); Dong-Yi Wu, New Taipei (CN); Brandon J. Guttersohn, Kansas City, MO (US)

(73) Assignee: Garmin Switzerland GmbH (CH)

( * ) Notice: Subject to any disclaimer, the term of this patent is extended or adjusted under 35 U.S.C. 154(b) by 174 days.

(21) Appl. No.: 15/909,089

(22) Filed: Mar. 1, 2018

(65) Prior Publication Data

US 2019/0269341 A1    Sep. 5, 2019

(51) Int. Cl.
    *A61B 5/1455*   (2006.01)
    *A61B 5/02*     (2006.01)
    *A61B 5/024*    (2006.01)
    *A61B 5/00*     (2006.01)

(52) U.S. Cl.
    CPC ...... *A61B 5/02433* (2013.01); *A61B 5/02438* (2013.01); *A61B 5/1455* (2013.01); *A61B 5/681* (2013.01); *A61B 2562/0238* (2013.01)

(58) Field of Classification Search
    None
    See application file for complete search history.

(56) References Cited

U.S. PATENT DOCUMENTS

2014/0361147 A1* 12/2014 Fei ............... G01J 1/0407
                                             250/206

OTHER PUBLICATIONS

Chung et al., Signal-enhancement reflective pulse oximeter with Fresnel lens, Optics Communications, Mar. 3, 2016.

* cited by examiner

*Primary Examiner* — Eric F Winakur
*Assistant Examiner* — Marjan Fardanesh
(74) *Attorney, Agent, or Firm* — Samuel M. Korte; Max M. Ali

(57) ABSTRACT

An electronic fitness device comprises an optical transmitter, a first lens, an optical receiver, and a second lens. The optical transmitter is operable to transmit an optical signal. The first lens covers at least a portion of the optical transmitter and is operable to direct the optical signal into the skin of a user in a first direction outward from a center of the electronic fitness device. The optical receiver is operable to receive optical signals modulated by the skin of the user and to generate a photoplethysmogram (PPG) signal resulting from the optical signal. The second lens covers at least a portion of the optical receiver and is operable to receive a modulated optical signal from the skin of the user in a second direction inward toward the center of the electronic fitness device and to direct the modulated optical signal toward the optical receiver.

19 Claims, 10 Drawing Sheets

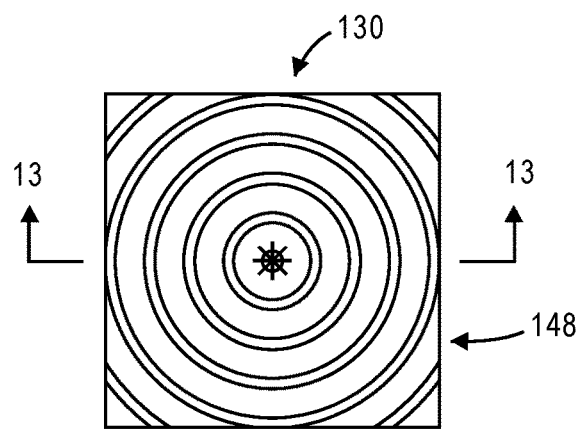
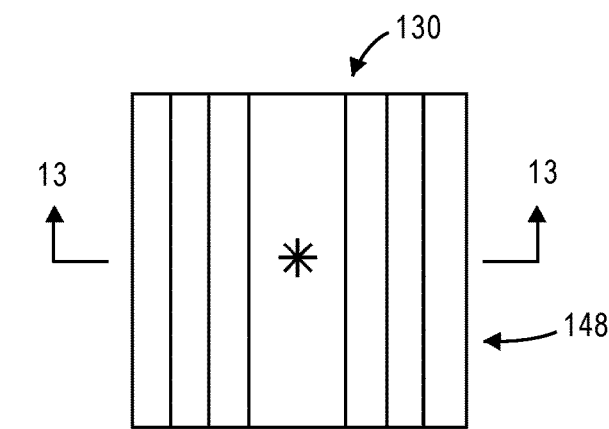
FIG. 12A  FIG. 12B
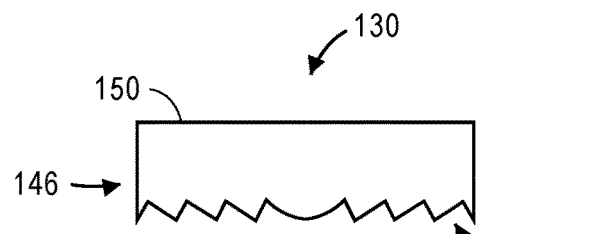
FIG. 13

ELECTRONIC FITNESS DEVICE WITH IMPROVED LENS CONFIGURATION

BACKGROUND

An electronic fitness device may provide optical cardiac monitoring of a user of the device. The user (wearer) may be any individual who wears the electronic device such that a housing of the electronic device is located proximate to skin of the individual (e.g., worn against the person's wrist, abdomen, leg, etc.). The cardiac monitoring may include physiological metrics and information such as a user's heart rate. The electronic fitness device may utilize a photoplethysmogram (PPG) signal to determine the cardiac monitoring information. The PPG signal is typically output by a photodiode and is commonly utilized to identify changes in the volume of blood in the skin proximate to the photodiode and is collected over a period of time encompassing many heart beats. The electronic fitness device may include optical devices, such as an optical transmitter, which emits an optical signal (light) into the user's skin, and an optical receiver, which receives reflections of the optical signal (light) from the skin and generates a PPG signal corresponding to the intensity of the received light. Typically, the electronic fitness device includes a housing and straps enabling it to be worn on the wrist, arm, leg, or torso, and the optical devices are positioned on the back, or bottom wall, of the housing to orient the optical devices to output and receive light from the user's skin when the device is worn. During operation, the optical signal travels on a roughly semicircular path directly from the optical transmitter to the optical receiver.

SUMMARY

Applicant has observed that there is a positive correlation between a distance that an optical signal travels through the user's skin and a reduction of noise components in the PPG signal. That is, a greater distance that the optical signal travels through the user's skin leads to a greater reduction of noise components in the PPG signal, which in turn, leads to greater accuracy in determining cardiac monitoring information of the user. Embodiments of the present technology provide an electronic fitness device for determining cardiac monitoring information which includes an optical transmitter, an optical receiver, and a lens configuration that transmits the optical signal through the user's skin in a direction outward from a center of the device and receives the optical signal in a direction inward toward the center of the device. This configuration creates a path for the optical signal that is generally oblong, or partially elliptical, and greater in length than the roughly semicircular path that the optical signal travels without the lens configuration.

An embodiment of the electronic fitness device broadly comprises a housing, an optical transmitter, a first lens, an optical receiver, and a second lens. The housing includes a bottom wall and one or more side walls. The optical transmitter is positioned in a first opening on the bottom wall and is operable to transmit an optical signal. The first lens covers at least a portion of the optical transmitter and is operable to direct the optical signal into the skin of a user in a first direction outward from a center of the electronic fitness device. The optical receiver is positioned in a second opening on the bottom wall and is operable to receive optical signals modulated by the skin of the user and to generate a photoplethysmogram (PPG) signal resulting from the optical signal. The second lens covers at least a portion of the optical receiver and is operable to receive a modulated optical signal from the skin of the user in a second direction inward toward the center of the electronic fitness device and to direct the modulated optical signal toward the optical receiver.

Another embodiment of the present technology provides an electronic fitness device broadly comprising a housing, an optical transmitter, a first lens, an optical receiver, and a second lens. The housing includes a bottom wall and one or more side walls. The optical transmitter is positioned in a first opening on the bottom wall and is operable to transmit an optical signal. The first lens covers the optical transmitter and includes a body and a lens element forming a monolithic unit with a center of the lens element being offset from a center of the body and a center of the first opening. The first lens is operable to direct the optical signal into the skin of a user in a first direction outward from a center of the electronic fitness device. The optical receiver is positioned in a second opening on the bottom wall and is operable to receive optical signals modulated by the skin of the user and to generate a photoplethysmogram (PPG) signal resulting from the optical signal. The second lens covers the optical receiver and includes a body and a lens element forming a monolithic unit with a center of the lens element offset from a center of the body and a center of the second opening. The second lens is operable to receive a modulated optical signal from the skin of the user in a second direction inward toward the center of the electronic fitness device and to direct the modulated optical signal toward the optical receiver.

Yet another embodiment of the present technology provides an electronic fitness device broadly comprising a housing, an optical transmitter, a first lens, an optical receiver, and a second lens. The housing includes a bottom wall and one or more side walls. The optical transmitter is positioned in a first opening on the bottom wall and is operable to transmit an optical signal. The first lens covers at least a portion of the optical transmitter and includes a center that is offset from a center of the optical transmitter. The first lens is operable to direct the optical signal into the skin of a user in a first direction outward from a center of the electronic fitness device. The optical receiver is positioned in a second opening on the bottom wall and is operable to receive optical signals modulated by the skin of the user and to generate a photoplethysmogram (PPG) signal resulting from the optical signal. The second lens covers at least a portion of the optical receiver and includes a center that is offset from a center of the optical receiver. The second lens is operable to receive a modulated optical signal from the skin of the user in a second direction inward toward the center of the electronic fitness device and to direct the modulated optical signal toward the optical receiver.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWING FIGURES

Embodiments of the present technology are described in detail below with reference to the attached drawing figures, wherein:

FIGS. 12A and 12B are bottom views of embodiments of the lens utilized with the electronic fitness device;

FIG. 13 is a side sectional view of the lens cut along the line 13-13 of FIGS. 12A and 12B;

Figure 18A:
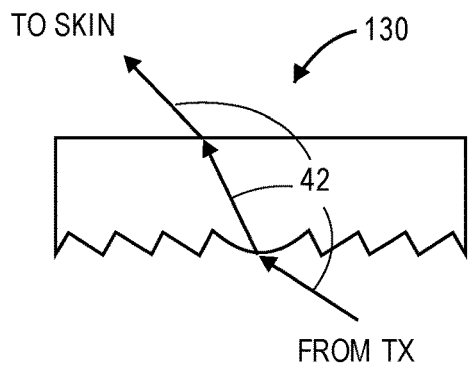
FIG. 18A is a schematic side view of the lens of FIGS. 12A and 12B depicting a path that the optical signal would take passing through the lens in a first direction.
Figure 18B:
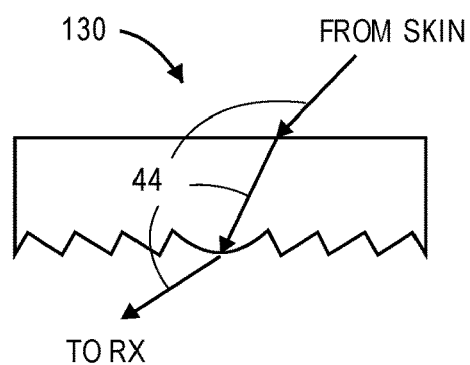
Figure 19:
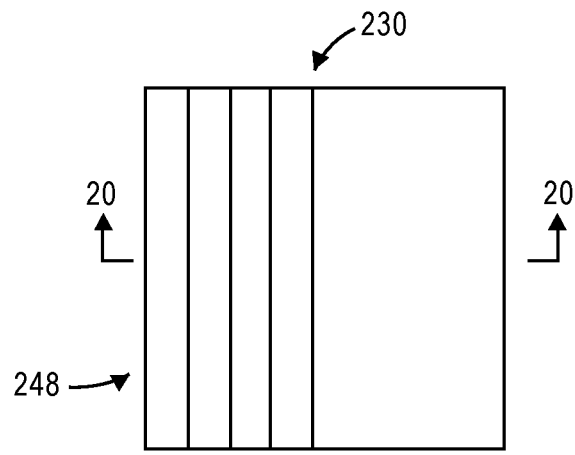
Figure 20:
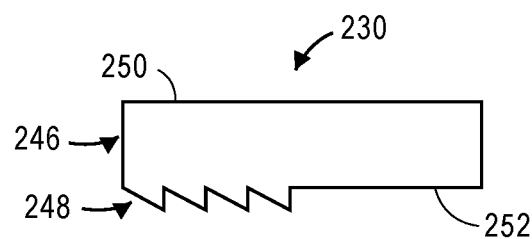
Figure 21:
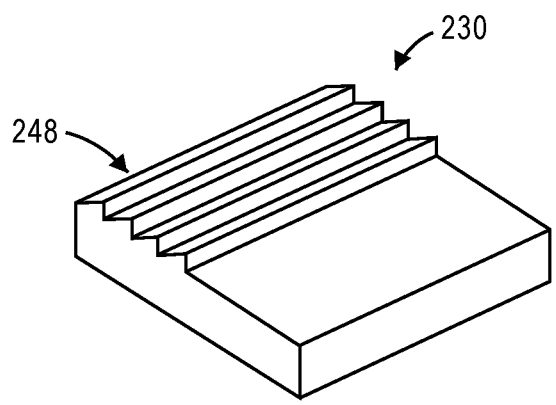

FIG. 18B a schematic side view of the lens of FIGS. 12A and 12B depicting a path that the optical signal would take passing through the lens in a second direction;

FIG. 19 is a bottom view of embodiments of the lens utilized with the electronic fitness device;

FIG. 20 is a side sectional view of the lens cut along the line 20-20 of FIG. 19; and FIG. 21 is a bottom perspective view of the lens of FIG. 19.

The drawing figures do not limit the present technology to the specific embodiments disclosed and described herein. The drawings are not necessarily to scale, emphasis instead being placed upon clearly illustrating the principles of the technology.

DETAILED DESCRIPTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the present technology. The following detailed description is, therefore, not to be taken in a limiting sense. The scope of the present technology is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
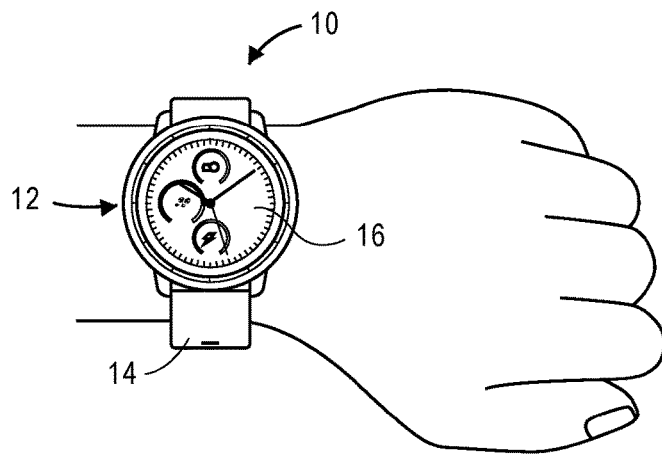
FIG. 1 is a top view of an electronic fitness device, constructed in accordance with various embodiments of the present technology, shown on a user's wrist.
Figure 2:
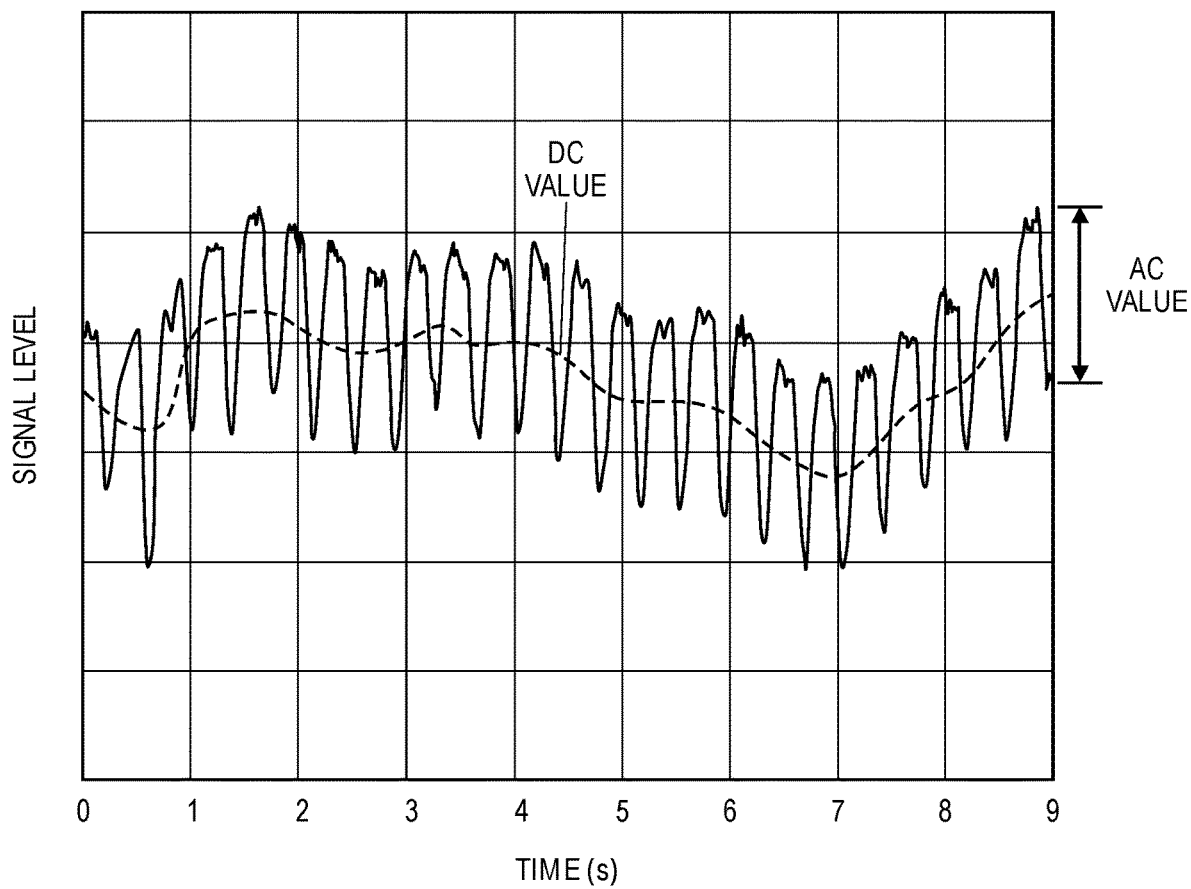
FIG. 2 is a plot of a photoplethysmogram (PPG) signal waveform that may be generated by the electronic fitness device over time.
Figure 3:
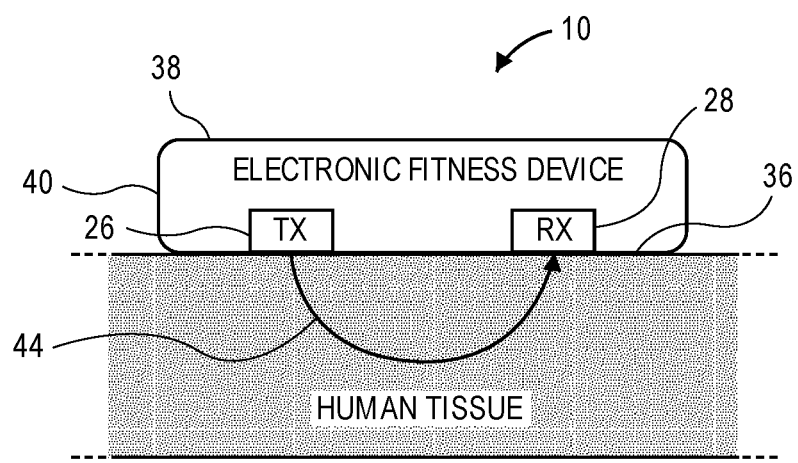
FIG. 3 is a schematic side sectional view of the electronic fitness device and a user's wrist depicting transmission of an optical signal through the skin and tissue of the user.
Figure 4:
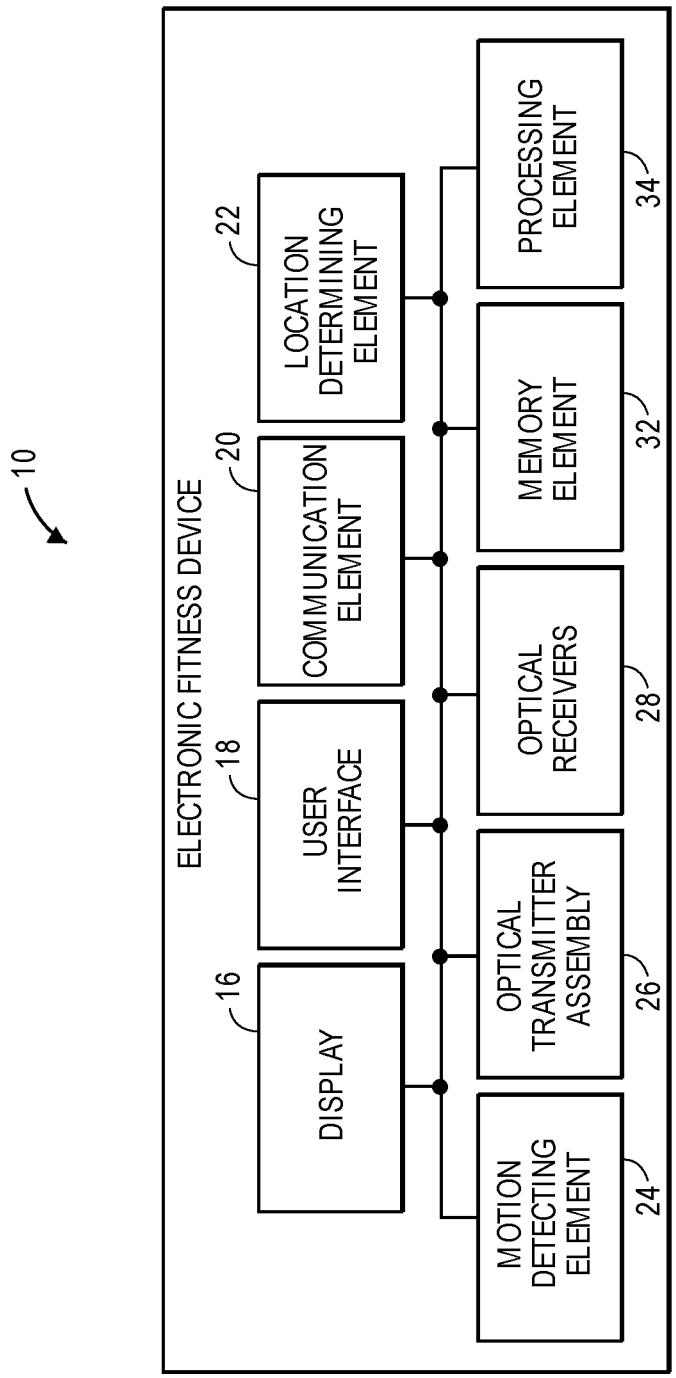
FIG. 4 is a schematic block diagram of various electronic components of the electronic fitness device.

Embodiments of the present technology provide an electronic fitness device that may be worn on a user's wrist, such as the electronic fitness device shown in FIG. 1, and provides optical cardiac monitoring by generating and utilizing photoplethysmogram (PPG) signals, such as the PPG signal shown as a waveform in FIG. 2. Cardiac monitoring may include determining information such as the user's pulse or heart rate, a pulse oximetry ("Pulse Ox") level (also known as a level of blood oxygen saturation, or SpO2), an estimated stress level, a maximum rate of oxygen consumption (VO2 max), or the like. Referring to FIG. 3, a PPG signal is based on an optical signal (light) emitted from an optical transmitter (TX) into the user's skin (human tissue) proximate to the optical transmitter (TX). The user (wearer) may be any individual who wears the electronic device such that a housing of the electronic device is located proximate to skin of the individual (e.g., worn against the person's wrist, abdomen, leg, etc.). The emitted optical signal penetrates the user's skin to a depth that ranging from tens of microns to several millimeters depending on a variety of criteria, such as the wavelength of transmitted light, presence of blood vessels and composition of the user's skin layers. A portion of the optical signal is reflected, or otherwise transferred, from the skin to an optical receiver (RX), typically a photodiode, that generates the PPG signal. The magnitude of the PPG signal is associated with an intensity of the received optical signal (light). The optical signal may be modulated, or otherwise modified, by the flow of blood through the vessels in the path of the optical signal. Specifically, the optical signal is modulated by the blood flow response to the beating of the user's heart, or the cardiac cycle. Thus, the optical signal received by the optical receiver (RX) has been modulated to include a cardiac component corresponding to the user's cardiac characteristics, which are associated with the user's heartbeat. In turn, the PPG signal generated by the optical receiver (RX) includes the cardiac component corresponding to the user's heartbeat. In addition to the cardiac component, the PPG signal includes undesirable components, such as a motion component resulting from motion of the user, noise components resulting from operation of the device and/or electronic circuitry of the optical receiver (RX), etc.

Generally, as seen in FIG. 2, the PPG signal waveform includes an AC value and a DC value. The AC value of the waveform is a moving peak-to-peak value, i.e., the local maximum minus the local minimum over successive small periods of time. The DC value is the moving average value, i.e., a mean value of the local maximum and the local minimum over successive small periods of time, of the waveform. In some implementations, the DC value is a lowpass-filtered PPG signal. In other implementations, the DC value is a signal formed by connecting and interpolating the local minima or maxima over small periods of time, of the waveform. Still referring to FIG. 2, the cardiac component of the PPG signal is typically a periodic, substantially sinusoidal waveform. A low-frequency AC noise, (e.g. motion component) tends to vary and may be included in the DC value, causing the PPG waveform to move up or down. Motion and various other high-frequency AC noise components tend to pollute the PPG signal and make the identification and extraction of the cardiac signal difficult. Some AC noise components, with frequencies approaching that of the cardiac component modulate the envelope of and/or otherwise distort the cardiac component. Generally, "AC value" corresponds to the cardiac component of the PPG signal. In environments where AC noise is present in the PPG signal, it is desirable to remove the AC noise from the PPG signal before estimating AC value.

Embodiments of the present technology will now be described in more detail with reference to the drawing figures. Referring initially to FIGS. 1 and 4-18, an electronic fitness device 10 with an improved lens configuration for providing PPG signals with reduced noise components is illustrated. An exemplary electronic fitness device 10 may be embodied by a smart watch or a fitness band that is typically worn on a user's wrist, but may also be embodied by bands or belts worn on the user's arm, leg, or torso. The user may be considered any individual who wears the electronic fitness device 10 such that a housing of the electronic device is located proximate to skin of the individual (e.g., worn against a person's wrist, abdomen, leg, etc.). Other examples of the electronic fitness device 10 may include smartphones, personal data assistants, or the like which include a surface, operable to retain optical devices, that can be pressed against the user's skin. The electronic fitness device 10 may broadly comprise a housing 12, a wrist band 14, a display 16, a user interface 18, a communication element 20, a location determining element 22, a motion detecting element 24, an optical transmitter 26, an optical receiver 28, a lens(es) 30, a memory element 32, and a processing element 34.

The housing 12 generally houses or retains other components of the electronic fitness device 10 and may include or be coupled to the wrist band 14. As seen in FIG. 3, the housing 12 may include a bottom wall 36, an upper surface 38, and at least one side wall 40 that bound an internal cavity (not shown in the figures). The bottom wall 36 may include a lower, outer surface that contacts the user's wrist while the user is wearing the electronic fitness device 10. The upper surface 38 opposes the bottom wall 36. In various embodiments, the upper surface 38 may further include an opening that extends from the upper surface to the internal cavity. In some embodiments, such as the exemplary embodiments shown in the figures, the bottom wall 36 of the housing 12 may have a round, circular, or oval shape, with a single circumferential side wall 40. In other embodiments, the bottom wall 36 may have a four-sided shape, such as a square or rectangle, or other polygonal shape, with the housing 12 including four or more sidewalls. The bottom wall 36 includes one or more openings through which one or more optical transmitter array(s) 26 emit or transmit an optical signal and one or more optical receiver(s) 28 receive reflections of the optical signal from the user's skin. The one or more openings within the bottom wall 36 may be covered by one or more lenses 30 through which the optical signal may be transmitted and received.

The display 16 generally presents the information mentioned above, such as time of day, current location, and the like. The display 16 may be implemented in one of the following technologies: light-emitting diode (LED), organic LED (OLED), Light Emitting Polymer (LEP) or Polymer LED (PLED), liquid crystal display (LCD), thin film transistor (TFT) LCD, LED side-lit or back-lit LCD, or the like, or combinations thereof. In some embodiments, the display 16 may have a round, circular, or oval shape. In other embodiments, the display 16 may possess a square or a rectangular aspect ratio which may be viewed in either a landscape or a portrait orientation. The electronic fitness device 10 may further include a lens that is positioned on an upper surface of the display 16 to enhance the visibility of the information shown on the display 16.

The user interface 18 generally allows the user to directly interact with the electronic fitness device 10 and may include pushbuttons, rotating knobs, or the like. In various embodiments, the display 16 may also include a touch screen occupying the entire display 16 or a portion thereof so that the display 16 functions as at least a portion of the user interface 18. The touch screen may allow the user to interact with the electronic fitness device 10 by physically touching, swiping, or gesturing on areas of the display 16.

The communication element 20 generally allows communication with external systems or devices. The communication element 20 may include signal and/or data transmitting and receiving circuits, such as antennas, amplifiers, filters, mixers, oscillators, digital signal processors (DSPs), and the like. The communication element 20 may establish communication wirelessly by utilizing radio frequency (RF) signals and/or data that comply with communication standards such as cellular 2G, 3G, 4G, LTE, or 5G, Institute of Electrical and Electronics Engineers (IEEE) 802.11 standard such as Wi-Fi, IEEE 802.16 standard such as WiMAX, Bluetooth™, or combinations thereof. In addition, the communication element 20 may utilize communication standards such as ANT, ANT+, Bluetooth™ low energy (BLE), the industrial, scientific, and medical (ISM) band at 2.4 gigahertz (GHz), or the like. Alternatively, or in addition, the communication element 20 may establish communication through connectors or couplers that receive metal conductor wires or cables which are compatible with networking technologies such as Ethernet. In certain embodiments, the communication element 20 may also couple with optical fiber cables. The communication element 20 may be in electronic communication with the memory element 32 and the processing element 34.

The location determining element 22 generally determines a current geolocation of the electronic fitness device 10 and may receive and process radio frequency (RF) signals from a global navigation satellite system (GNSS) such as the global positioning system (GPS) primarily used in the United States, the GLONASS system primarily used in the Soviet Union, or the Galileo system primarily used in Europe. The location determining element 22 may accompany or include an antenna to assist in receiving the satellite signals. The antenna may be a patch antenna, a linear antenna, or any other type of antenna that can be used with location or navigation devices. The location determining element 22 may include satellite navigation receivers, processors, controllers, other computing devices, or combinations thereof, and memory. The location determining element 22 may process a signal, referred to herein as a "location signal", from one or more satellites that includes data from which geographic information such as the current geolocation is derived. The current geolocation may include coordinates, such as the latitude and longitude, of the current location of the electronic fitness device 10. The location determining element 22 may communicate the current geolocation to the processing element 34, the memory element 32, or both.

Although embodiments of the location determining element 22 may include a satellite navigation receiver, it will be appreciated that other location-determining technology may be used. For example, cellular towers or any customized transmitting radio frequency towers can be used instead of satellites may be used to determine the location of the electronic fitness device 10 by receiving data from at least three transmitting locations and then performing basic triangulation calculations to determine the relative position of the device with respect to the transmitting locations. With such a configuration, any standard geometric triangulation algorithm can be used to determine the location of the electronic fitness device 10. The location determining element 22 may also include or be coupled with a pedometer, accelerometer, compass, or other dead-reckoning components which allow it to determine the location of the device 10. The location determining element 22 may determine the current geographic location through a communications network, such as by using Assisted GPS (A-GPS), or from another electronic fitness device. The location determining element 22 may even receive location data directly from a user.

The motion detecting element 24 generally detects movement of the electronic fitness device 10 and may include accelerometers, tilt sensors, inclinometers, gyroscopes, combinations thereof, or other devices including piezoelectric, piezoresistive, capacitive sensing, or micro electromechanical systems (MEMS) components. The motion detecting element 24 may sense motion along one axis of motion or multiple axes of motion. Motion detecting element 24 that sense motion along three orthogonal axes, such as X, Y, and Z, are often used. In various embodiments, the motion detecting element 24 may measure the acceleration, such as acceleration due to the gravitation (G) force, of the user and may output the measured data in a digital binary format.

In some embodiments, the optical transmitter 26 may include a photonic generator, such as a light-emitting diode (LED), a modulator, a top emitter, an edge emitter, or the like. The photonic generator receives an electrical input signal (from other circuitry such as the processing element 34) that may be a control signal, such as an electric voltage or electric current that is analog or digital, or data, either of which is indicative of activating or energizing the optical transmitter 26 to transmit (emit) an optical signal 42 having a desired amplitude, frequency, and duration. The photonic generator transmits the optical signal 42, which is electromagnetic radiation having a particular wavelength (the optical signal 42) in the visible light spectrum, i.e., approximately 400 nanometers (nm) to approximately 700 nm or in the infrared spectrum, i.e., approximately 700 nm to approximately 1 millimeter (mm). In additional or alternative embodiments, the photonic generator transmits electromagnetic radiation having a wavelength in the range of approximately 1000 nm to approximately 1500 nm. The wavelength is generally determined by, or varies according to, the material from which the photonic generator is formed. The optical signal 42 corresponds to the electrical input signal in amplitude, frequency, and duration. The optical signal 42 may comprise a sequence of pulses, a periodic or non-periodic waveform, a constant level for a given period of time, or the like, or combinations thereof.

In other embodiments, the optical transmitter 26 may include a driver circuit, with electronic circuitry such as amplifier and an optional filter, electrically coupled to the photonic generator. The driver circuit may receive the electrical input signal or control signal. The driver circuit may generate an electric voltage or electric current to the photonic generator, which in turn, transmits (emits) the optical signal 42.

The optical receiver 28 generally receives a modulated optical signal 44 (i.e., an optical signal 42 modulated by the skin of the user) and, in response, generates the PPG signal. In some embodiments, the optical receiver 28 may include a photodetector, such as a photodiode, a phototransistor, a photoresistor, a phototube, or the like. The photodetector receives electromagnetic radiation having a range of wavelengths (typically including the wavelength generated by the optical transmitter 26) and in response, generates the PPG signal, comprising an electric current, an electric voltage, or other electrical parameter that corresponds to the intensity of the modulated optical signal 44 in amplitude and frequency. In some situations, the PPG signal generated by the optical receiver 28 may include characteristics or components resulting from, or related to, the wavelength of the optical signal 42.

In other embodiments, the optical receiver 28 may include the photodetector electrically coupled to an amplifier circuit followed by an analog-to-digital converter (ADC). The photodetector may receive electromagnetic radiation having multiple wavelengths and in response, may generate an output signal, comprising an electric current, an electric voltage, or other electrical parameter that corresponds to the modulated optical signal 44 in amplitude and frequency. The amplifier circuit receives the output signal from the photodetector and amplifies it to produce an amplified output signal that is analog and communicated to the ADC. The ADC samples the amplified output signal and converts it to a corresponding stream of digital data which is the PPG signal.

The bottom wall 36 of the housing 12 may include at least a first opening in which the optical transmitter 26 is positioned and a second opening in which the optical receiver 28 is positioned. In some implementations, the housing 12 and the wrist band 14 may be positioned such that the optical transmitter 26 and the optical receiver 28 are located substantially over (i.e. most proximally to) one of the wrist bones. For example, the optical components may be positioned substantially over the ulna bone or substantially over the radius bone.

The electronic fitness device 10 may include a first lens 30A associated with the optical transmitter 26 and a second lens 30B associated with the optical receiver 28. Typically, the first lens 30A and the second lens 30B have the same structure or construction. In some embodiments, the first lens 30A may have a first structure, while the second lens 30B may have a second, different structure. In other embodiments, only one lens 30 may be used, such that a lens 30 may be associated with the optical transmitter 26 and not the optical receiver 28, or a lens 30 may be associated with the optical receiver 28 and not the optical transmitter 26.

The lenses 30 may be constructed from glass, polycarbonates, polymers, or the like, or combinations thereof. Each lens 30 includes a body 46 and a lens element 48. The body 46 includes an upper surface 50 and a lower surface 52. In some embodiments, the upper surface 50 is flat, or planar, and smooth, and the lower surface 52 includes the lens element 48. In other embodiments, the lower surface 52 is flat, or planner, and smooth, and the upper surface 50 includes the lens element 48. The lens 30 may include an additional layer positioned above or below the lens element 48 such that both the upper surface 50 and the lower surface 52 are flat, or planar, and smooth. For example, in embodiments where the upper surface 50 includes the lens element 48, the upper surface 50 may include a finishing layer of glass, polycarbonates, polymers, or the like, positioned above the lens element 48 that results in the upper most surface of lens 30 being flat, or planner, and smooth. Each lens 30 may include four side surfaces, such as the exemplary lens 30 shown in FIGS. 5A-7B, giving the lens 30 a square or rectangular shape. Optionally, the corners of the square or rectangular shape may be rounded. In other embodiments, each lens 30 may include a signal side surface, giving the lens 30 a round, oval, elliptical, or similar shape. Furthermore, each lens 30 includes a center, such as a geometric center, (marked with an "X" in FIGS. 5A and 5B) which may be defined, or determined, to have coordinates including a midpoint of a width dimension and a midpoint of a length dimension.

The lens element 48 may be etched on, molded on, formed on, or coupled to the upper surface 50 or the lower surface 52 of the body 46, such that the lens 30 and lens element 48 are a monolithic unit.

Figure 5A:
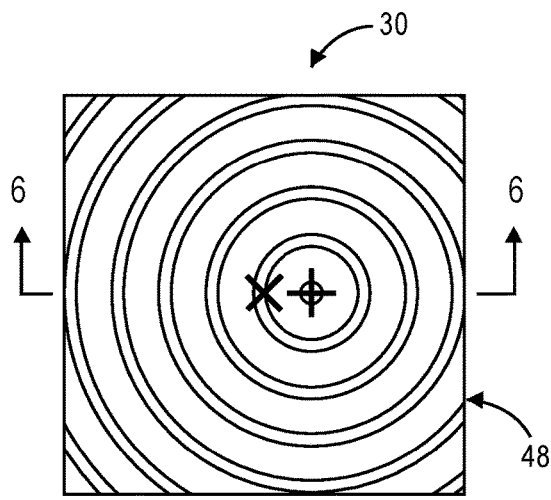
FIGS. 5A and 5B are bottom views of embodiments of a lens utilized with the electronic fitness device, the lens including a body and a lens element with indications of a center of the body and a center of the lens element.
Figure 5B:
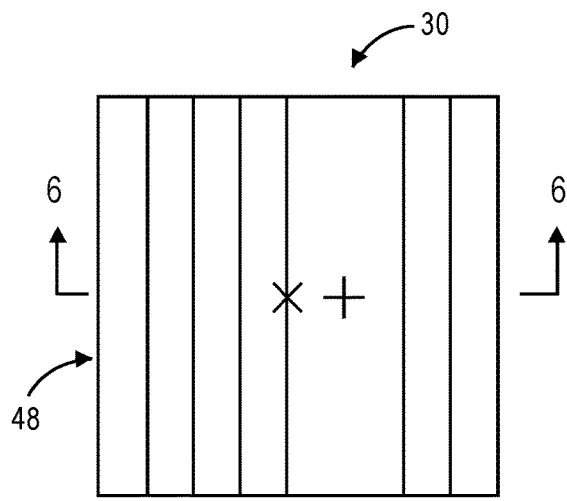

In embodiments, the lens element 48 may include three-dimensional features along the X and Y dimensions as well as the Z dimension, such that the lens element 48 has a depth, or a height. The features of the lens element 48 may include a plurality of concentric circular sections, where a center of the concentric sections is a center of the lens element 48, a plurality of vertical or horizontal sections extending between opposing sides of the lens element 48, or a plurality of diagonal sections extending between adjacent sides of the lens element 48. In the exemplary embodiment of FIGS. 5A and 5B, if the lens 30 has a width of 10 units and a length of 10 units, then the center of the lens 30 may have coordinates of (5 units, 5 units) in the x-y plane. In some embodiments, the spacing between the plurality of concentric sections of the lens element 48 may be different or equal (uniform), as shown in FIG. 5A. Similarly, the spacing between the plurality of vertical sections of the lens element 48 may be different or equal (uniform), as shown in FIG. 5B.

Figure 6:
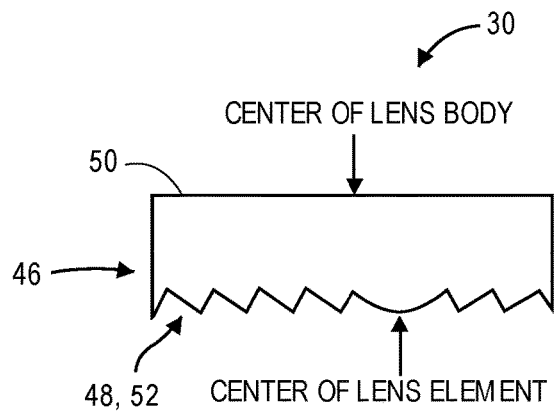
FIG. 6 is a side sectional view of the lens cut along the line 6-6 of FIGS. 5A and 5B.
Figure 7A:
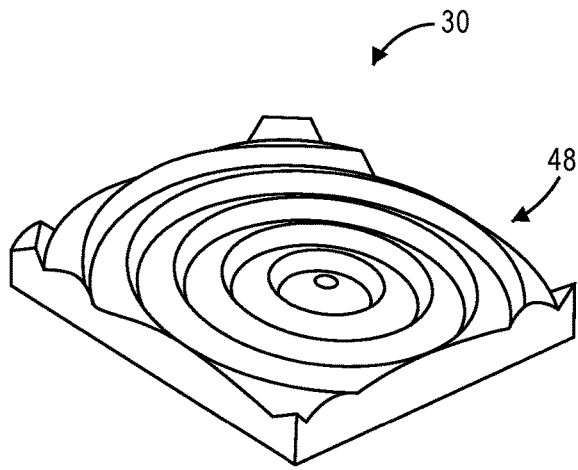
FIGS. 7A and 7B are bottom perspective views of the lens of FIGS. 5A and 5B, respectively.
Figure 7B:
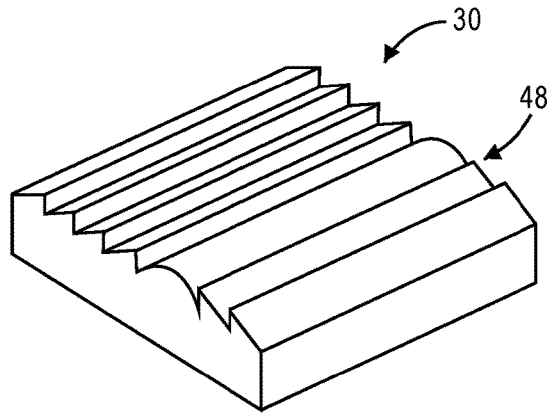
Figure 8:
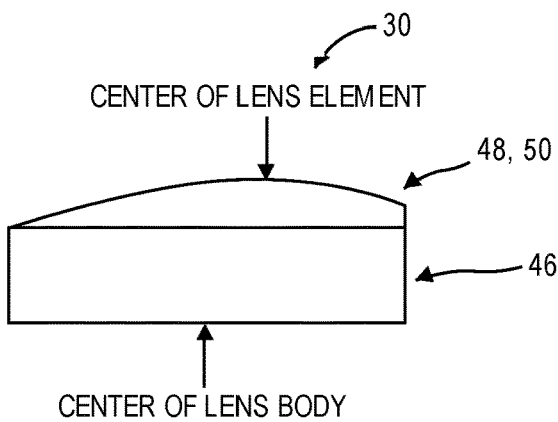
FIG. 8 is a side view of another embodiment of the lens.

In addition, the lens element 48 includes a center (marked with a "+" in FIGS. 5A and 5B) which may be defined, or determined, to have coordinates including a midpoint of the lens element 48 features, such as a plurality of concentric lines or a plurality of vertical lines. Thus, the lens 30 illustrated in FIGS. 5A-7B includes a lens element 48 having a center (marked "+" in FIGS. 5A and 5B) that is offset from the center of the lens 30 (marked "X" in FIGS. 5A and 5B). The lens element 48 and the features thereof may be positioned on the upper surface 50 or the lower surface 52 of each lens 30 such that the center of the lens element 48 is offset from the center of the lens 30. The lens element 48 may be positioned on the upper surface 50 or the lower surface 52 such that the center of the lens element 48 has coordinates of (7, 5)—thus having an offset from the center of the lens 30 in the positive X direction with a distance of 2 units. In fact, the center of the lens element 48 may be offset from the center of the lens 30 in any direction and at any distance that is possible on the upper surface 50. In addition, as shown in FIGS. 6 and 7A-7B, the lens element 48 may include ridges and valleys along the Z dimension. Exemplary embodiments of the lens 30 with the lens element 48 may include a Fresnel lens or similar compact lens, wherein the center of the Fresnel pattern is offset from the center of the lens 30. Alternatively, in embodiments, the lens 30 may be embodied by a plano-convex lens wherein the lens element 48 includes a parabolic or hemispheric convex portion with an apex positioned on the upper surface 50. As shown in FIG. 8, the apex, or center, of the convex portion may be offset from the center of the lens 30.

Figure 9A:
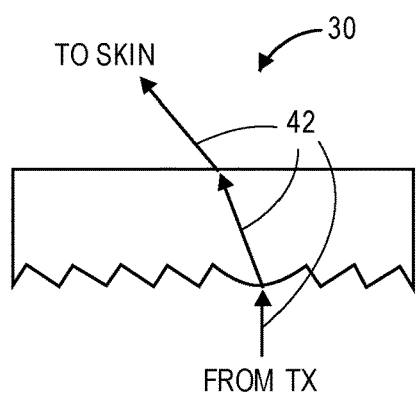
FIG. 9A is a schematic side view of the lens of FIGS. 5A and 5B depicting a path that an optical signal would take passing through the lens in a first direction.

In embodiments, a center of the optical transmitter 26 may correspond to (align with) a center of the lens 30 and is offset from a center of the lens element 48 of the lens 30 such that an optical signal 42 output by the optical transmitter 26 may enter the lens 30 travelling in a first direction and exit the lens 30 travelling in a different direction. For example, as shown in FIG. 9A, an optical signal 42 output by the optical transmitter 26 may travel in a first direction toward the lens element 48 and travel in a second direction that is offset from the first direction after the optical signal 42 is transmitted through lens element 48. The optical signal 42 may travel in the second direction through the lens body 46 from the lower surface 52 toward the planar upper surface 50. The optical signal 42 may travel through the planar upper surface 50 toward the user's skin in a third direction that is offset from the second direction after exiting the lens 30.

Figure 9B:
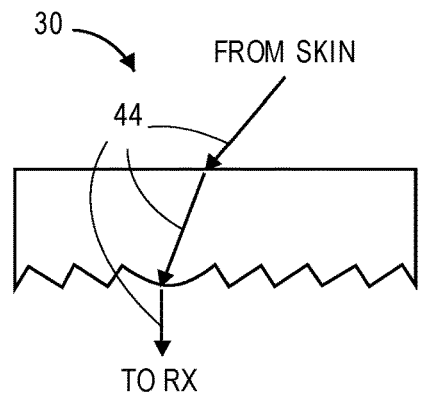
FIG. 9B is a schematic side view of the lens of FIGS. 5A and 5B depicting a path that the optical signal would take passing through the lens in a second direction.

In embodiments, a center of the optical receiver 28 may correspond to (align with) a center of the lens 30 and is offset from a center of the lens element 48 of the lens 30 such that a modulated optical signal 44 reflected from the user's skin may enter the lens 30 travelling in a first direction and exit the lens 30 travelling in a different direction towards the optical receiver 28. For example, as shown in FIG. 9B, the modulated optical signal 44 reflected from the user's skin may travel in a first direction toward lens 30 and travel in a second direction that is offset from the first direction after the modulated optical signal 44 passes through the planar upper surface 50. The modulated optical signal 44 may travel in the second direction through the lens body 46 from the upper surface 50 toward the lower surface 52, which may include the lens element 48. The modulated optical signal 44 may travel through the lens element 48 toward the optical receiver 28 after exiting lens 30 in a third direction that is offset from the second direction. Although other modulated optical signals may enter the lens 30 from directions other than the first direction, the lens element 48 may reflect the other modulated optical signals out of the lens 30 through upper surface 50 or any direction other than the third direction such that only modulated optical signals that enter the lens 30 from the first direction pass through to the optical receiver 28.

Figure 10:
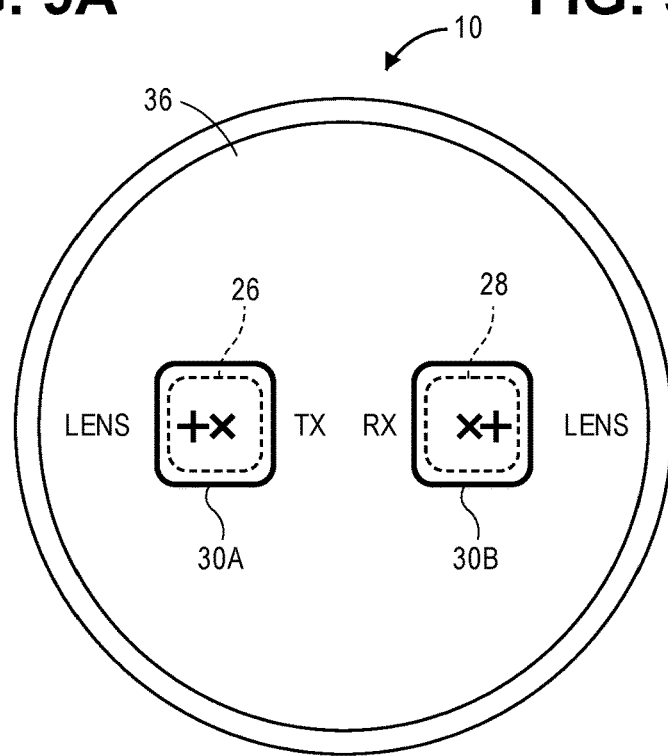
FIG. 10 is a schematic bottom view of the electronic fitness device illustrating a first lens covering an optical transmitter and a second lens covering an optical receiver.
Figure 11A:
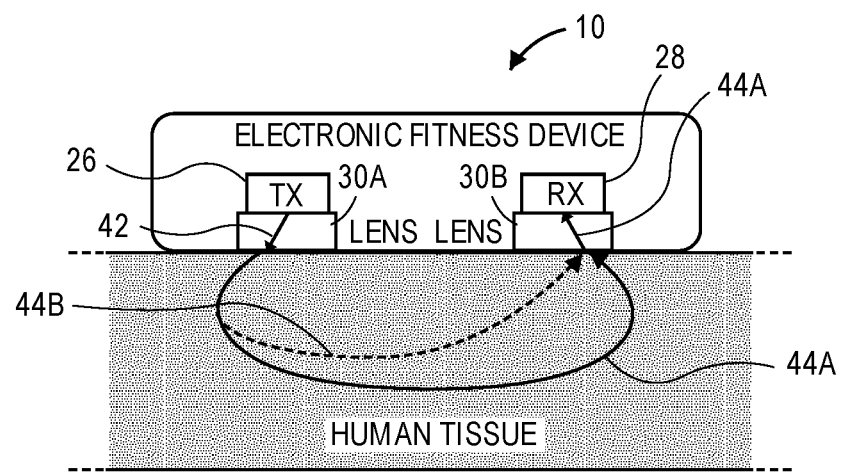
FIGS. 11A and 11B are schematic side sectional views of two embodiments illustrating paths that portions of a modulated optical signal travel from the first lens to the second lens.

As shown in FIGS. 10 and 11A, in embodiments, a first lens 30A may be positioned on or along the bottom wall 36 directly over the optical transmitter 26, such that the first lens 30A covers the optical transmitter 26. The first lens 30A may be oriented and positioned over the optical transmitter 26 such that the center of the lens element 48 (marked with a "+" in FIG. 10) of the body 46 of the first lens 30A is positioned outward from the center of the optical transmitter 26 (marked with an "X" in FIG. 10) and radially outward from the center of the bottom wall 36. With this configuration, the first lens 30A directs the optical signal 42 output by the optical transmitter 26 out from the bottom wall 36 and away from the center of the electronic fitness device 10 toward the side wall 40. Thus, in embodiments, the lens element 48 of the first lens 30A directs optical signal 42 output by the optical transmitter 26 in a direction that is away from optical receiver 28. In some embodiments as shown, the body 46 of the first lens 30A may have a slightly larger area or size than the optical transmitter 26 such that the first lens 30A covers the optical transmitter 26 and additional areas. In other embodiments not shown, the area of the body 46 of the first lens 30A may be roughly the same size as the area of the optical transmitter 26.

The second lens 30B may be positioned on or along the bottom wall 36 directly over the optical receiver 28, such that the second lens 30B covers the optical receiver 28. The second lens 30B may be oriented and positioned over the optical receiver 28 such that the center of the lens element 48 (marked with a "+" in FIG. 10) of the body 46 of the second lens 30B is positioned outward from the center of the optical receiver 28 (marked with an "X" in FIG. 10) and radially outward from the center of the bottom wall 36. With this configuration, lens element 48 of the second lens 30B receives the modulated optical signal 44 in a direction coming from the side wall 40 opposing the optical transmitter 26 and traveling toward the center of the electronic fitness device 10. Thus, in embodiments, the lens element 48 of second lens 30B may receive the modulated optical signal 44 to be passed through to the optical receiver 28 from a direction that is towards optical transmitter 26. In other embodiments, the lens element 48 of second lens 30B may receive the modulated optical signal 44 from any direction and allow the received modulated optical signal 44 to pass through to the optical receiver 28. Like the first lens 30A and the optical transmitter 26, the area of the body 46 of the second lens 30B may be slightly larger than the optical receiver 28 and overlap the optical receiver 28 or the area of the body 46 of the second lens 30B may be roughly the same size as the area of the optical receiver 28.

Figure 11B:
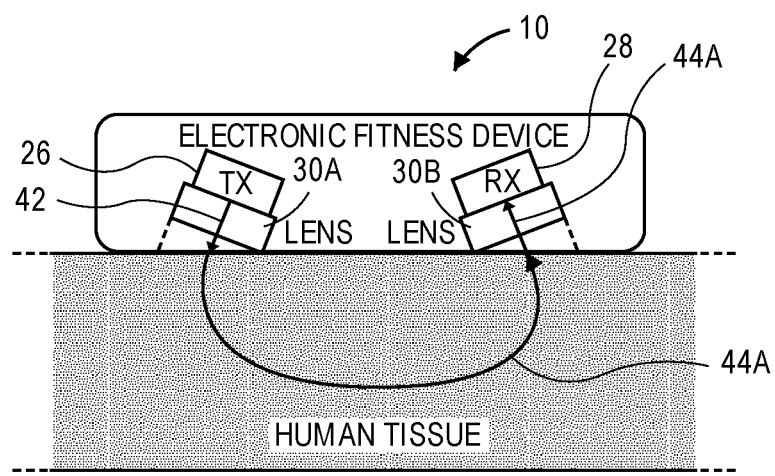

Similarly, as shown in FIGS. 10 and 11B, in embodiments, a first lens 30A may be positioned within an opening of or along the bottom wall 36 and tilted such that the angle of the first lens 30A points in a direction in which the optical signal 42 is transmitted through the first lens 30A. The first lens 30A may be positioned directly over the optical transmitter 26 (from a bottom view perspective), such that the first lens 30A covers the optical transmitter 26. The second lens 30B may be positioned within an opening of or along the bottom wall 36 and tilted such that the angle of the second lens 30B points in a direction from which the modulated optical signal 44A is received through the second lens 30B. In some embodiments, the bottom wall 36 may be shaped such that the first lens 30A and the second lens 30B may be positioned on or along the bottom wall 36. For example, the bottom wall 36 may have a partially curved shape where the first lens 30A is positioned along the bottom wall 36 pointing away from the optical receiver 28 (without being located within an opening of or along the bottom wall 36) and the first lens 30A may be positioned directly over the optical transmitter 26 (from a bottom view perspective), such that the first lens 30A covers the optical transmitter 26. Similarly, the second lens 30B may be positioned along the bottom wall 36 such that the second lens 30B either points down (and the optical receiver 28 may receive the modulated optical signal 44A traveling towards that area of the bottom wall 36) or away from the optical transmitter 26 (and the optical receiver 28 may receive the modulated optical signal 44A traveling towards that area of the bottom wall 36).

The memory element 32 may be embodied by devices or components that store data in general, and digital or binary data in particular, and may include exemplary electronic hardware data storage devices or components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 32 may be embedded in, or packaged in the same package as, the processing element 34. The memory element 32 may include, or may constitute, a "computer-readable medium". The memory element 32 may store the instructions, code, code statements, code segments, software, firmware, programs, applications, apps, services, daemons, or the like that are executed by the processing element 34. The memory element 32 may also store settings, data, documents, sound files, photographs, movies, images, databases, and the like.

The processing element 34 may include electronic hardware components such as processors, microprocessors (single-core or multi-core), microcontrollers, digital signal processors (DSPs), field-programmable gate arrays (FPGAs), analog and/or digital application-specific integrated circuits (ASICs), or the like, or combinations thereof. In some embodiments, the processing element 34 may also include ADC circuitry. The processing element 34 may generally execute, process, or run instructions, code, code segments, code statements, software, firmware, programs, applications, apps, processes, services, daemons, or the like. The processing element 34 may also include hardware components such as finite-state machines, sequential and combinational logic, and other electronic circuits that can perform the functions necessary for the operation of the current invention. The processing element 34 may be in electronic communication with the other electronic components through serial or parallel links that include universal busses, address busses, data busses, control lines, and the like. Furthermore, the processing element 34 may include multiple physically separated but logically and electronically connected functional blocks.

The processing element 34 may be operable, configured, or programmed to perform the following functions through hardware, software, firmware, or combinations thereof. The processing element 34 generates the electrical input signal or control signal, which may include an electric voltage or electric current that is constant or variable, analog or digital, or data, as a single number or a stream of numbers, and communicates the signal to the optical transmitter 26 in order to control the optical transmitter 26.

The optical receiver 28 generates the PPG signal based on the received modulated optical signal 44 and the processing element 34 receives the PPG signal from the optical receiver 28. In some embodiments, the processing element 34 may sample the analog PPG signal from the optical receiver 28 to produce a digital form of the PPG signal. In other embodiments, the processing element 34 may receive the digital form of the PPG signal from the optical receiver 28. Once the processing element 34 is in possession of the PPG signal, it may perform one or more of a plurality of signal conditioning and/or processing functions on the PPG signal to determine cardiac monitoring information such as the user's heart rate. Furthermore, the processing element 34 may also control the display 16 to display the cardiac monitoring information.

The electronic fitness device 10 may operate as follows. The user may desire to determine his cardiac information, such as heart rate or pulse oximetry. He may utilize the user interface 18 to direct the processing element 34 to begin the process of determining a heart rate, the pulse oximetry, or other cardiac information. Alternatively, or additionally, the processing element 34 may have an operating mode in which it automatically initiates the process of determining the heart rate, pulse oximetry, or other cardiac information, on a periodic basis.

The processing element 34 generates the electrical input signal and communicates it to the optical transmitter 26. Referring to FIG. 11A, the optical transmitter 26 transmits the optical signal 42 through the first lens 30A, which includes a lens element 48 that directs the optical signal 42 into the user's skin in a first direction away from the center of the electronic fitness device 10. The optical signal 42 is modulated by the user's skin, such as the upper skin layers of the user's wrist. At least a portion of the modulated optical signal 44 travels through the user's skin and surrounding tissue toward the second lens 30B and the optical receiver 28. For example, a first portion of the modulated optical signal 44A may travel through the user's skin and is reflected from the skin toward the electronic fitness device 10 such that the first portion of the modulated optical signal 44A travels toward the second lens 30B in a second direction coming inward toward the center of the electronic fitness device 10. A second portion of the modulated optical signal 44B may travel through the user's skin and is reflected from the skin toward the electronic fitness device 10 such that the second portion of the modulated optical signal 44B travels toward the second lens 30B in a third direction coming from the first lens 30A (i.e., the modulated optical signal 44B travels a shorter path than the modulated optical signal 44A). The second lens 30B may include a lens element 48 that directs the first portion of the modulated optical signal 44A, which enters the second lens 30B from the second direction, through the body of the second lens 30B toward the optical receiver 28, such that such that a significant amount of the modulated optical signal 44A is received by the optical receiver 28. The lens element 48 of the second lens 30B may reflect the second portion of the modulated optical signal 44B, which enters the second lens 30B from the third direction, out of the second lens 30B through an upper surface 50 of the second lens 30B such that a significant amount of the modulated optical signal 44B is not received by the optical receiver 28 and only the first portion of the modulated optical signal 44A that enters the second lens 30B from the second direction passes through to and is received by the optical receiver 28. The optical receiver 28 generates a PPG signal using the received first portion of the modulated optical signal 44A. The PPG signal is communicated to the processing element 34, which may perform one or more of a plurality of signal conditioning and/or processing functions on the PPG signal to determine cardiac information such as the user's heart rate or pulse oximetry. The processing element 34 may also control the display 16 to display the determined cardiac information.

With the lens 30 configuration shown in FIGS. 5-11A, the first lens 30A includes a lens element 48 that directs the optical signal 42 transmitted by the optical transmitter 26 in the first direction outward and away from the center of the electronic fitness device 10 and the second lens 30B includes a lens element 48 that rejects optical signals received from a direction other than the direction of the modulated optical signal 44A from the side wall 40, inward toward the center of the electronic fitness device 10 such that only the modulated optical signal 44A is received by the optical receiver 28. This creates a path for the modulated optical signal 44A to travel that is generally oblong, or partially elliptical, as shown in FIG. 11A, and that is greater in length than the shortest path or the shorter path of the modulated optical signal 44B. As shown in FIG. 3, a short path of the modulated optical signal 44 may roughly equal to a distance from a center of the optical transmitter 26 to a center of the optical receiver 28. The paths of the modulated optical signals 44A, 44B shown in FIG. 11A are greater in distance than the distance between the center of the optical transmitter 26 and the center of the optical receiver 28. A modulated optical signal 44 that travels a greater distance may result in a PPG signal that has a higher signal-to-noise ratio (SNR) or a higher signal-to-motion noise ratio (SMNR) than it would without the lens 30 configuration—thereby enabling processing element 34 to determine more accurate cardiac information, such as a user's heart rate or pulse oximetry. In embodiments, the electronic fitness device 10 may include only one of the first lens 30A and the second lens 30B. In such embodiments, the modulated optical signal 44 would still travel a greater distance than traveled by a modulated optical signal that does not pass through a lens element 48. For example, if only the first lens 30A is utilized, the lens element 48 of the first lens 30A causes the optical signal 42 to be transmitted from the electronic fitness device 10 in the first direction outward from the center of the bottom wall 36 resulting in the first portion of the modulated optical signal 44A traveling a greater distance on the transmit side than illustrated in FIG. 3. If only the second lens 30B is utilized, the lens element 48 of the second lens 30B reflects modulated optical signals 44 such that only the modulated optical signal 44 that is received from the second direction inward from the side wall 40 passes through to and is received by the optical receiver 28, which results in the modulated optical signal 44 received by the optical receiver 28 traveling a greater distance on the receive side than illustrated in FIG. 3.

A second embodiment of the electronic fitness device 100 is shown in FIGS. 12A-18. The electronic fitness device 100 may comprise the housing 12, the wrist band 14, the display 16, the user interface 18, the communication element 20, the location determining element 22, the motion detecting element 24, the optical transmitter 26, the optical receiver 28, the memory element 32, and the processing element 34, all as described above.

The electronic fitness device 100 also includes a first lens 130A associated with the optical transmitter 26 and a second lens 130B associated with the optical receiver 28. Typically, the first lens 130A and the second lens 130B have the same structure or construction. In some embodiments, the first lens 130A may have a first structure, while the second lens 130B may have a second, different structure. In other embodiments, only one lens 130 may be used, such that a lens 130 may be associated with the optical transmitter 26 and not the optical receiver 28, or a lens 130 may be associated with the optical receiver 28 and not the optical transmitter 26.

The lenses 130 may be constructed from glass, polycarbonates, polymers, or the like, or combinations thereof. Each lens 130 includes a body 146 and a lens element 148. The body 146 includes an upper surface 150 and a lower surface 152. As described above, in some embodiments, the upper surface 150 is flat, or planar, and smooth, and the lower surface 152 includes the lens element 148. In other embodiments, the lower surface 152 is flat, or planner, and smooth, and the upper surface 150 includes the lens element 148. The lens 130 may include an additional layer positioned above or below the lens element 148 such that both the upper surface 150 and the lower surface 152 are flat, or planar, and smooth. For example, in embodiments where the upper surface 150 includes the lens element 148, the upper surface 150 may include a finishing layer of glass, polycarbonates, polymers, or the like, positioned above the lens element 148 that results in the upper most surface of lens 130 being flat, or planner, and smooth. Each lens 130 may include four side surfaces, such as the exemplary lens 130 shown in FIGS. 12A-14B, giving the lens 130 a square or rectangular shape. Optionally, the corners of the square or rectangular shape may be rounded. In other embodiments, each lens 30 may include a signal side surface, giving the lens 130 a round, oval, elliptical, or similar shape.

Figure 14A:
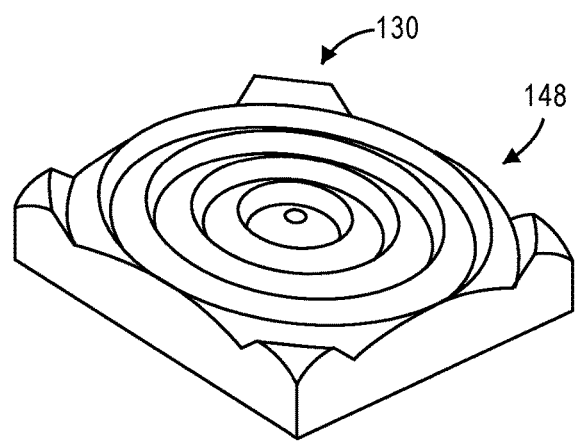
FIGS. 14A and 14B are bottom perspective views of the lens of FIGS. 12A and 12B, respectively.
Figure 14B:
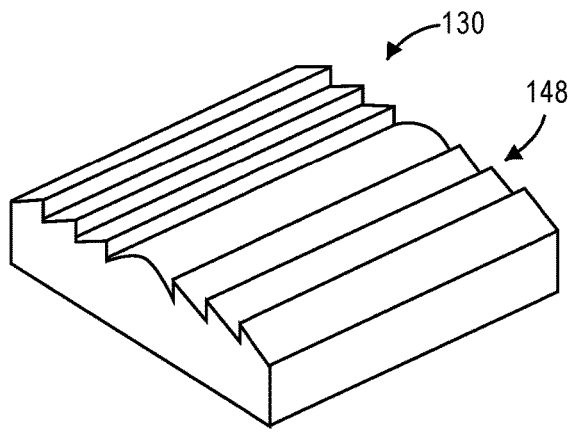

The lens element 148 may be etched on, molded on, formed on, or coupled to the upper surface 150 of the body 146, such that the lens 130 is a monolithic unit. The lens element 148 is typically three-dimensional with features along the X and Y dimensions as well as the Z dimension, such that the lens element 148 has a depth, or a height. An exemplary lens element 148 may include a plurality of concentric circular sections, or vertical sections, as shown in FIGS. 12A-14B. Unlike the lens 30 illustrated in FIGS. 5A-7B, the lens 130 illustrated in FIGS. 12A-14B includes a lens element 148 having a center that corresponds to (aligned with) the center of the body 146 of the lens 130. In addition, as shown in FIGS. 13 and 14A-14B, the lens element 148 includes ridges and valleys along the Z dimension. Exemplary embodiments of the lens 130 with the lens element 148 may include a Fresnel lens or similar compact lens.

Figure 15:
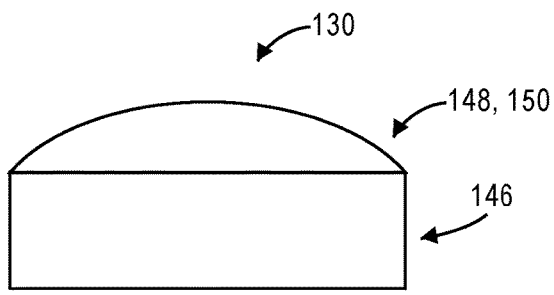
FIG. 15 is a side view of another embodiment of the lens.

Alternatively, as shown in FIG. 15, the lens 130 may be embodied by a plano-convex lens wherein the lens element 148 includes a parabolic or hemispheric convex portion with an apex positioned on the upper surface 150. In addition, the centers of the body 146 and the lens element 148 are aligned with one another.

Figure 16:
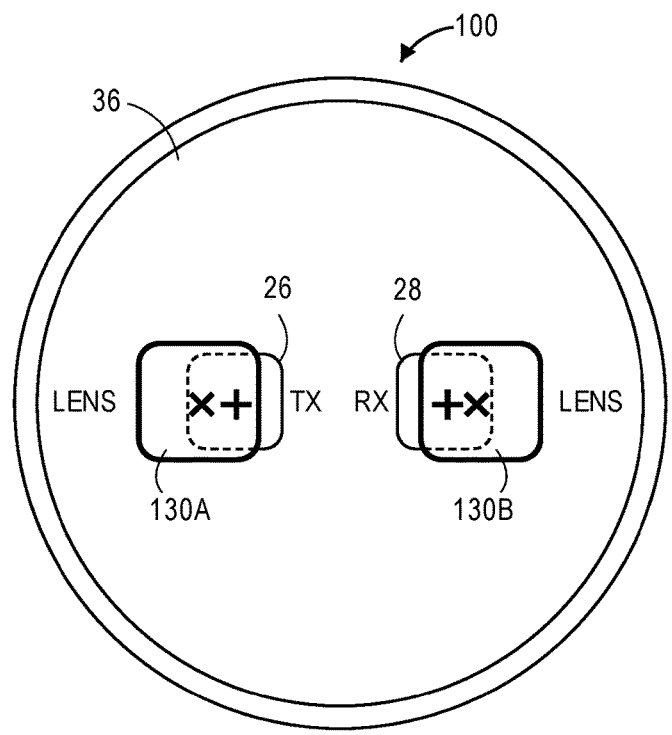
FIG. 16 is a schematic bottom view of the electronic fitness device illustrating a first lens covering at least a portion of the optical transmitter and a second lens covering at least a portion of the optical receiver.
Figure 17A:
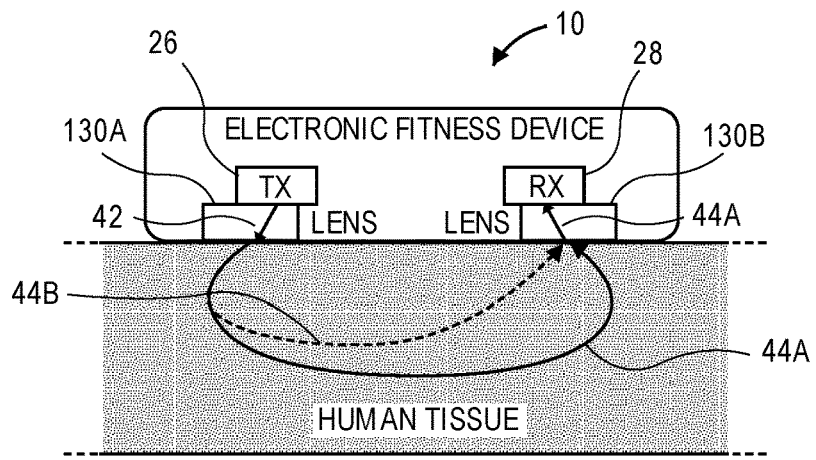
FIGS. 17A and 17B are schematic side sectional views of two embodiments illustrating paths that portions of a modulated optical signal travel from the first lens to the second lens.

In embodiments, a center of the optical transmitter 26 may be offset from a center of the lens 130 that corresponds to (aligns with) a center of the lens element 148 of the lens 130 such that an optical signal 42 output by the optical transmitter 26 may enter the lens 130 travelling in a first direction and exit the lens 130 travelling in a different direction. For example, as shown in FIGS. 16 and 17A, the first lens 130A may be positioned on or along the bottom wall 36 such that the center of the lens 130A (marked with an "X" in FIG. 16) is offset from a center of the optical transmitter 26 (marked with a "+" in FIG. 16). The center of the optical transmitter 26 may be aligned with a center of the first opening in which the optical transmitter 26 is positioned. The center of the first lens 130A, which corresponds to (aligns with) a center of the lens element 148 of the first lens 130A, may be positioned outward, toward the side wall 40, from the center of the optical transmitter 26. In some embodiments as shown, the first lens 130A may have a slightly larger area or size than the area of the optical transmitter 26 such that the first lens 130A covers the optical transmitter 26 and additional areas. In other embodiments not shown, the area of the body 146 of the first lens 130A may be roughly the same size as the area of the optical transmitter 26.

In embodiments, a center of the optical receiver 28 may be offset from a center of the lens 130 that corresponds to (aligns with) a center of the lens element 148 of the lens 130 such that a modulated optical signal 44 reflected from the user's skin may enter the lens 130 travelling in a first direction and exit the lens 130 travelling in a different direction towards the optical receiver 28. For example, the second lens 130B is positioned on or along the bottom wall 36 such that the center of the lens 130B (marked with an "X" in FIG. 16) is offset from a center of the optical receiver 28 (marked with an "+" in FIG. 16). The center of the optical receiver 28 may be aligned with a center of the second opening in which the optical receiver 28 is positioned. The center of the second lens 130B, which corresponds to (aligns with) a center of the lens element 148 of the second lens 130B, is positioned outward, toward the side wall 40, from the center of the optical transmitter 26, or radially outward from the center of the bottom wall 36. In some embodiments as shown, the second lens 130B may have a slightly larger area or size than the area of the optical receiver 28 such that the second lens 130B covers the optical receiver 28 and additional areas. In other embodiments not shown, the area of the body 146 of the second lens 130B may be roughly the same size as the area of the optical receiver 28.

As shown in FIG. 18A, an optical signal 42 output by the optical transmitter 26 may travel in a first direction toward the lens element 148 of lens 130A and travel through the lens element 148 in a second direction that is offset from the first direction due to the relative offset position of the first lens 130A over the optical transmitter 26. The optical signal 42 may travel in the second direction through the lens body 46 from the lower surface 152 toward the planar upper surface 150 of the lens 130. The optical signal 42 transmitted from the optical transmitter 26 passes through the upper surface 150 of lens 130 toward the user's skin in a third direction that is offset from the second direction after exiting lens 130.

As shown in FIG. 18B, a modulated optical signal 44 reflected from the user's skin may travel in a first direction toward lens 130B and travel in a second direction that is offset from the first direction after the modulated optical signal 44 passes through the planar upper surface 150 of the second lens 130B. The modulated optical signal 44 may travel in the second direction through the lens body 46 of the second lens 130B from the upper surface 150 toward the lower surface 152, which may include the lens element 148. The modulated optical signal 44 may travel through the lens element 148 toward the optical receiver 28 after exiting lens 130B in a third direction that is offset from the second direction due to the relative offset position of the second lens 130B over the optical receiver 28. Although other optical signals may enter the second lens 130B from directions other than the first direction, the lens element 148 of the second lens 130B and the relative offset between the center of the second lens 130B and the center of the optical receiver 28 may reflect the other optical signals out of lens 130B through the upper surface 150 or any direction other than the third direction such that only modulated optical signals that enter the lens 130 from the first direction pass through to the optical receiver 28.

The electronic fitness device 100 may operate as follows. The user may desire to determine his cardiac information, such as heart rate or pulse oximetry. He may utilize the user interface 18 to direct the processing element 34 to begin the process of determining the heart rate, the pulse oximetry, or other cardiac information. Alternatively, or additionally, the processing element 34 may have an operating mode in which it automatically initiates the process of determining the heart rate, pulse oximetry, or other cardiac information, on a periodic basis.

The processing element 34 generates the electrical input signal and communicates it to the optical transmitter 26. Referring to FIG. 17A, the optical transmitter 26 transmits the optical signal 42 through first lens 130, the center of which is offset with respect to the center of the optical transmitter 26, that directs the optical signal 42 into the user's skin in a first direction away from the center of the electronic fitness device 10. The lens element 148 of the first lens 130A and the offset between the first lens 130A and the optical transmitter 26 direct the optical signal 42 in the first direction. The optical signal 42 is modulated by the user's skin, such as the upper skin layers of the user's wrist. At least a portion of the modulated optical signal 44 travels through the user's skin and surrounding tissue toward the second lens 130B and the optical receiver 28. For example, a first portion of the modulated optical signal 44A may travel through the user's skin and is reflected from the skin toward the electronic fitness device 10 such the first portion of the modulated optical signal 44A travels toward the second lens 130B in a second direction coming inward toward the center of the electronic fitness device 10. A second portion of the modulated optical signal 44B may travel through the user's skin and is reflected from the skin toward the electronic fitness device 10 such that the second portion of the modulated optical signal 44B travels toward the second lens 130B in a third direction coming from the first lens 130A (i.e., the modulated optical signal 44B travels a shorter path than the modulated optical signal 44A). The lens element 148 of the second lens 130B and the offset between the second lens 130B and the optical receiver 28 may direct the first portion of the modulated optical signal 44A, which enters second lens 130B from the second direction, through the body of the second lens 130B toward the optical receiver 28, such that a significant amount of the modulated optical signal 44A is received by the optical receiver 28. The lens element 148 of the second lens 130B and the offset between the second lens 130B and the optical receiver 28 may reflect the second portion of the modulated optical signal 44B, which enters the second lens 130B from the third direction, out of the second lens 130B through an upper surface 50 of the second lens 130B such that a significant amount of the modulated optical signal 44B is not received by the optical receiver 28 and only the first portion of the modulated optical signal 44A that enters the second lens 130B from the second direction passes through to and is received by the optical receiver 28. The optical receiver 28 generates a PPG signal using the received first portion of the modulated optical signal 44A. The PPG signal is communicated to the processing element 34, which may perform one or more of a plurality of signal conditioning and/or processing functions on the PPG signal to determine cardiac monitoring information such as the user's heart rate or pulse oximetry. The processing element 34 may also control the display 16 to display the determined cardiac information.

With the lens 130 configuration shown in FIGS. 12A-18, the lens element 148 of the first lens 130A and the offset between the first lens 130A and the optical transmitter 26 direct the optical signal 42 transmitted by the optical transmitter 26 in the first direction outward and away from the center of the electronic fitness device 10. And, lens element 148 of the second lens 130B and the offset between the second lens 130B and the optical receiver 28 may reject modulated optical signals received from a direction other than the direction of the modulated optical signal 44A from the side wall 40, inward toward the center of the electronic fitness device 10 such that only the modulated optical signal 44A is received by the optical receiver 28. This creates a path for the modulated optical signal 44A to travel that is generally oblong, or partially elliptical, as shown in FIG. 17A, and that is greater in length than the shortest path or the shorter path of the modulated optical signal 44B. The paths of the modulated optical signals 44A and 44B shown in FIG. 17A are greater in distance than the distance between the center of the optical transmitter 26 and the center of the optical receiver 28. A modulated optical signal 44 that travels a greater distance may result in a PPG signal that has a higher signal-to-noise ratio (SNR) or a higher signal-to-motion noise ratio (SMNR) than it would without the lens 30 configuration—thereby enabling processing element 34 to determine more accurate cardiac information, such as a user's heart rate or pulse oximetry.

Figure 17B:
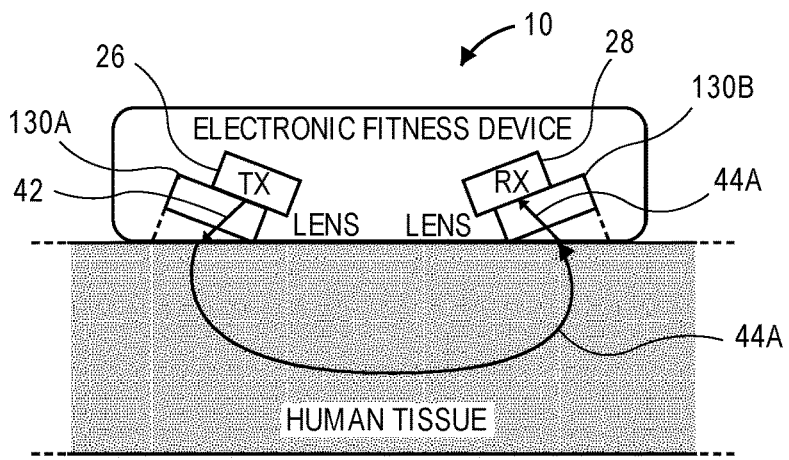

Similarly, as shown in FIG. 17B, in embodiments, a first lens 130A may be positioned within an opening of or along the bottom wall 36 and tilted such that the angle of the first lens 130A points in a direction in which the optical signal 42 is transmitted through the first lens 130A. The first lens 130A may be positioned directly over the optical transmitter 26, such that the first lens 130A covers the optical transmitter 26. The second lens 130B may be positioned within an opening of or along the bottom wall 36 and tilted such that the angle of the second lens 130B points in a direction from which the modulated optical signal 44A is received through the second lens 30B. In some embodiments, the bottom wall 36 may be shaped such that the first lens 130A and the second lens 130B may be positioned on or along the bottom wall 36. For example, the bottom wall 36 may have a partially curved shape where the first lens 130A is positioned along the bottom wall 36 pointing away from the optical receiver 28 (without being located within an opening of or along the bottom wall 36) and the first lens 130A may be positioned directly over the optical transmitter 26 (from a bottom view perspective), such that the first lens 130A covers the optical transmitter 26. Similarly, the second lens 130B may be positioned along the bottom wall 36 such that the second lens 130B either points down (and the optical receiver 28 may receive the modulated optical signal 44 traveling towards that area of the bottom wall 36) or away from the optical transmitter 26 (and the optical receiver 28 may receive the modulated optical signal 44A traveling towards that area of the bottom wall 36).

In some embodiments, a portion of a lens may include a lens element. For example, as shown in FIGS. 19-21, a lens 230 may include a lens element 248 on half of an upper surface 250 or a lower surface 252 of a body 246 of lens 230. The lens element 248 may be etched on, molded on, formed on, or coupled to the upper surface 250 or the lower surface 252 of the body 246, such that the lens 230 and lens element 248 are a monolithic unit. The lens element 248 may include three-dimensional features along the X and Y dimensions as well as the Z dimension, such that the lens element 248 has a depth, or a height. As shown in FIGS. 19-21, the features of the lens element 248 may include a plurality of vertical or horizontal sections extending between opposing sides of the lens element 248 on half of a lower surface 252 of the body 246. In other embodiments, the features of the lens element 248 may include a plurality of concentric circular sections or a plurality of diagonal sections extending between adjacent sides of the lens element 248.

Although the technology has been described with reference to the embodiments illustrated in the attached drawing figures, it is noted that equivalents may be employed and substitutions made herein without departing from the scope of the technology as recited in the claims.

What is claimed is:
1. An electronic fitness device comprising:
a housing including a bottom wall and one or more side walls;
an optical transmitter positioned in a first opening on the bottom wall and operable to transmit an optical signal;
a first lens covering at least a portion of the optical transmitter and including a lens element operable to direct the optical signal into the skin of a user in a first direction outward from a center of the electronic fitness device;

an optical receiver positioned in a second opening on the bottom wall and operable to receive optical signals modulated by the skin of the user and generate a photoplethysmogram (PPG) signal resulting from the received optical signal; and a second lens covering at least a portion of the optical receiver and including a lens element operable to receive the optical signals modulated by the skin of the user from a second direction inward toward the center of the electronic fitness device and direct the modulated optical signal toward the optical receiver;

wherein the first lens includes a body, the body and the lens element of the first lens forming a monolithic unit with a center of the lens element offset from a center of the body and a center of the first opening; and wherein the second lens includes a body, the body and the lens element of the second lens forming a monolithic unit with a center of the lens element offset from a center of the body and a center of the second opening.

2. The electronic fitness device of claim 1, wherein the modulated optical signal received by the optical receiver travels a path whose width is greater than a distance between a center of the optical transmitter and a center of the optical receiver.

3. The electronic fitness device of claim 1, wherein the center of the body of the first lens is aligned with a center of the optical transmitter, and wherein the center of the lens element of the first lens is positioned outward from the center of the optical transmitter and away from the optical receiver.

4. The electronic fitness device of claim 1, wherein the center of the body of the second lens is aligned with a center of the optical receiver, and wherein the center of the lens element of the second lens is positioned outward from the center of the optical receiver and away from the optical transmitter.

5. The electronic fitness device of claim 1, wherein the lens element of each of the first and second lenses includes a plurality of concentric circular sections such that a center of the sections is the center of the lens element.

6. The electronic fitness device of claim 1, wherein a center of the first lens is positioned outward from a center of the optical transmitter and a center of the second lens is positioned outward from a center of the optical receiver.

7. The electronic fitness device of claim 1, wherein the lens element of each of the first and second lenses includes a plurality of vertical sections such that a center of the sections is the center of the lens element.

8. The electronic fitness device of claim 1, further comprising a processing element in electronic communication with the optical transmitter and the optical receiver, the processing element operable to: control the optical transmitter to transmit the optical signal, receive the PPG signal from the optical receiver, and determine cardiac information of the user based on the received PPG signal.

9. An electronic fitness device comprising:

a housing including a bottom wall and one or more side walls;

an optical transmitter positioned in a first opening on the bottom wall and operable to transmit an optical signal;

a first lens covering the optical transmitter, the first lens including a body and a lens element forming a monolithic unit with a center of the lens element offset from a center of the body and a center of the first opening, the first lens operable to direct the optical signal into the skin of a user in a first direction outward from a center of the electronic fitness device;

an optical receiver positioned in a second opening on the bottom wall and operable to receive optical signals modulated by the skin of the user and generate a photoplethysmogram (PPG) signal resulting from the received optical signal; and a second lens covering the optical receiver, the second lens including a body and a lens element forming a monolithic unit with a center of the lens element offset from a center of the body and a center of the second opening, the second lens operable to receive the optical signals modulated by the skin of the user in a second direction inward toward the center of the electronic fitness device and direct the modulated optical signal toward the optical receiver.

10. The electronic fitness device of claim 9, wherein the modulated optical signal received by the optical receiver travels a path whose width is greater than a distance between a center of the optical transmitter and a center of the optical receiver.

11. The electronic fitness device of claim 9, wherein the center of the body of the first lens is aligned with a center of the optical transmitter and a center of the first opening, and wherein the center of the lens element of the first lens is positioned outward from the center of the optical transmitter and a center of the second opening.

12. The electronic fitness device of claim 9, wherein the center of the body of the second lens is aligned with a center of the optical receiver, and wherein the center of the lens element of the second lens is positioned outward from the center of the optical receiver.

13. The electronic fitness device of claim 9, wherein the lens element of each of the first and second lenses includes a plurality of concentric circular sections such that a center of the sections is the center of the lens element.

14. The electronic fitness device of claim 9, further comprising a processing element in electronic communication with the optical transmitter and the optical receiver, the processing element operable to:

control the optical transmitter to transmit the optical signal, receive the PPG signal from the optical receiver, and determine cardiac information of the user based on the received PPG signal.

15. An electronic fitness device comprising:

a housing including a bottom wall and one or more side walls;

an optical transmitter positioned in a first opening on the bottom wall and operable to transmit an optical signal;

a first lens covering at least a portion of the optical transmitter and including a center that is offset from a center of the first opening, the first lens including a body, the body and the lens element of the first lens forming a monolithic unit, and the first lens operable to direct the optical signal into the skin of a user in a first direction outward from a center of the electronic fitness device;

an optical receiver positioned in a second opening on the bottom wall and operable to receive optical signals modulated by the skin of the user and generate a photoplethysmogram (PPG) signal resulting from the optical signal; and a second lens covering at least a portion of the optical receiver and including a center that is offset from a center of the first opening, the second lens including a body, the body and the lens element of the first lens forming a monolithic unit, and the second lens operable to receive a modulated optical signal from the skin of the user in a second direction inward toward the center of the electronic fitness device and direct the modulated optical signal toward the optical receiver.

16. The electronic fitness device of claim 15, wherein the modulated optical signal received by the optical receiver travels a path whose width is greater than a distance between a center of the optical transmitter and a center of the optical receiver.

17. The electronic fitness device of claim 15, wherein the center of the first lens is positioned outward from the center of the optical transmitter, and wherein the center of the second lens is positioned outward from the center of the optical receiver.

18. The electronic fitness device of claim 15, wherein each of the first and second lenses includes a plurality of concentric circular sections positioned on an upper surface of the lens.

19. The electronic fitness device of claim 15, further comprising a processing element in electronic communication with the optical transmitter and the optical receiver, the processing element operable to:
  control the optical transmitter to transmit the optical signal,
  receive the PPG signal from the optical receiver, and
  determine cardiac information of the user based on the received PPG signal.

* * * * *